United States Patent [19]

Helwing

[11] Patent Number: 4,532,335

[45] Date of Patent: Jul. 30, 1985

[54] PREPARATION OF KETENE ACETALS BY REARRANGEMENT OF ALLYL AND SUBSTITUTED ALLYL ACETALS

[75] Inventor: Robert F. Helwing, San Jose, Calif.

[73] Assignee: SRI International, Menlo Park, Calif.

[21] Appl. No.: 473,027

[22] Filed: Mar. 7, 1983

[51] Int. Cl.$^3$ .......................................... C07D 319/00
[52] U.S. Cl. .................... 549/335; 568/596
[58] Field of Search ...................... 549/335; 568/596

[56] References Cited

U.S. PATENT DOCUMENTS 3,829,504 8/1974 Hall et al. ............................ 549/453
4,304,767 12/1981 Heller et al. ........................ 549/443

*Primary Examiner*—Ethel G. Love
*Attorney, Agent, or Firm*—Limbach, Limbach & Sutton

[57] ABSTRACT

Allyl acetals and substituted allyl acetals are rearranged to produce ketene acetals by heating the acetals in a solution of an alkali metal alkoxide in an ethylene amine.

5 Claims, No Drawings

PREPARATION OF KETENE ACETALS BY REARRANGEMENT OF ALLYL AND SUBSTITUTED ALLYL ACETALS

DESCRIPTION

1. Technical Field

This invention is directed to a method for rearranging allyl acetals and substituted allyl acetals to produce ketene acetals at high conversions and high purities of the ketene acetal product.

2. Background Art

It has been proposed to produce polymers which are bioerodible and are suitable as carriers or matrices for drugs and other beneficial agents used for therapeutic purposes and which, upon contact with the environment in which they are used, degrade and release the drug or other biologically active agent, by polymerizing a mixture of a polyol and a ketene acetal having a functionality greater than 1. Polymers of this kind and methods for producing the precursor ketene acetals are disclosed in U.S. Pat. No. 4,304,767. In this patent several methods for preparing the precursor ketene acetals are proposed. Among the proposals is the proposal to produce the ketene acetal by isomerization of allyl and substituted allyl acetals. In the rearrangement methods proposed, conversion of the allyl acetal to ketene acetal is far from complete and the ketene acetal product contains impurities which are very difficult to remove from the rearrangement reaction product.

Pursuant to the method of the present invention, allyl acetals are rearranged to ketene acetals and conversions of the order of 95% of theoretical are obtained.

BRIEF DESCRIPTION OF THE INVENTION

Pursuant to the present invention an allyl acetal or a substituted allyl acetal is added to a solution of an alkali metal alkoxide in an ethylene amine. The resulting mixture is heated to about 100° C. and held at that temperature for a period of several hours to several days depending upon the substituent in the substituted allyl acetal. Very high conversions of the allyl acetals to ketene acetals are obtained. Highly purified ketone acetals are separated from the ketene product by crystallization and/or distillation.

DETAILED DESCRIPTION OF THE PREFERRED EMBODIMENTS

The following examples describe in detail the procedure followed in rearranging allyl acetals to ketene acetals pursuant to the method of the present invention.

EXAMPLE 1

0.1782 mole of potassium tertiary butoxide and 100 milliliters of ethylene diamine are placed in a 200 milliliter three-necked round bottom flask under protection of an inert atmosphere to which a reflux condenser is attached. The potassium tertiary butoxide dissolves rapidly in the ethylene diamine.

0.0849 mols of diallylidene pentaerythritol is then added to the contents of the flask while under an inert atmosphere. The flask and contents are then heated to 100° C. and held at that temperature for 16 hours.

The reaction mixture was doused into water at 1000 ml water to 100 ml reaction mixture, the aqueous solution being basic in pH from the amine and butoxide, and then extracted with pentane, dried over anhydrous $K_2CO_3$ and 17 grams of ketene product having the formula

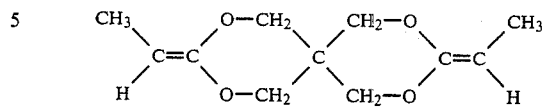

were recovered following evaporation of the pentane. Gas chromatographic analysis of the ketene product indicated a purity of 97.1%.

A second run was made in which the same materials were used in the same relative proportions, except that the quantity of each material was 15 times as great as in the first run, and 243 grams of the ketene reaction product were obtained.

The crude ketene product was purified by dissolving it in pentane and then cooling the solution in a dry-ice-/acetone mixture to a temperature about $-10°$ C. Ketene acetal crystals were formed and settled out. The crystals were then subjected to vacuum distillation and a purified ketene product was obtained.

EXAMPLE 2

Dimethallylidene pentaerythritol was rearranged to a diketene acetal according to the following reaction

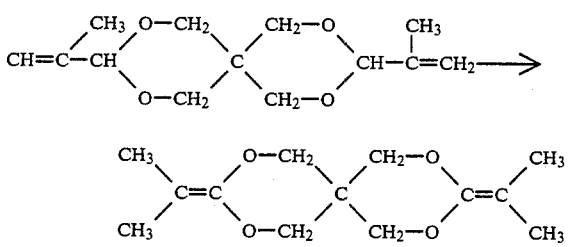

The dimethallylidene pentaerythritol, if not readily available may be prepared by reaction of 2 mols of methacrolein with 1 mol of pentaerythritol.

0.312 mols of potassium tertiary butoxide, 0.104 mols dimethallylidene pentaerythritol, and 150 milliliters of ethylene diamine were placed in a three-necked round bottom flask under an argon atmosphere. The flask was equipped with a reflux condenser system. The flask and contents were heated to 100° C. and held at that temperature for seven days. At the end of that time the reaction mixture was cooled to room temperature and stirred into 1000 milliliters of water. A white flocculated mass of crystals formed and floated to the top of the water phase which has a basic pH from the amine and butoxide. The crystals were filtered off, dissolved in pentane and anhydrous $K_2CO_3$ added to remove water. The pentane solution was cooled to subzero temperature using a mixture of dry ice and acetone. Crystals were formed and separated from the pentane solution. The crystals were then distilled under vacuum to recover a purified ketene product.

In the foregoing examples the allyl acetal starting materials were diallylidene acetals and were rearranged to diketene acetals. Acetals having the general formula

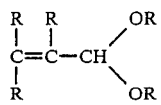

in which the R groups are lower alkyl groups are more readily converted to ketene acetals at high yields by the process of the invention than are higher alkyl substituted diallyl acetals.

Alkali metal alkoxides other than the exemplified alkoxide may be used. Alkali metal ethoxides, propoxides and butoxides are effective. Rubidium and cesium alkoxides as well as those of lithium, sodium and potassium are effective in the process but are obviously less attractive from the standpoint of cost.

Ethylene amines having the formula

in which n is 0 to 3 may be used instead of the ethylene diamine exemplified.

The temperature at which the rearrangement is carried out is conveniently 100° C. but temperatures about 100° C. up to the boiling point of the ethyleneamine component may be employed.

The quantity of butoxide employed should be slightly greater than one mole of butoxide for each molar part of allyl radical contained in the allyl acetal starting material. For example with the acetals employed in the examples, about 1.05–1.5 moles of butoxide per mole of the acetal are employed.

The ketene reaction mixture may be treated to recover a very highly purified ketene by stirring the reaction product into several times its volume of water, extracting with pentane, drying the pentane extract with anhydrous $K_2CO_3$, evaporating off the pentane, (the concentrated product can be stored without degradation at subzero temperature until ready to proceed with purification) dissolving the concentrated ketene in reagent grade pentane, cooling the pentane solution to about −10° C., collecting the crystals formed and vacuum distilling the crystals to obtain a highly purified (99%+) ketene acetal.

The invention described herein was made in the course of or under National Institute of Health Contract No. 1-HD-7-2826 with the U.S. Department of Health, Education and Welfare.

I claim:

1. The method of rearranging allyl acetals and substituted allyl acetals to produce ketene acetals which comprises heating said acetals in a solution of an alkali metal alkoxide in an ethylene amine.
2. The method of claim 1 wherein the alkali metal alkoxide is a potassium alkoxide.
3. The method of claim 1 wherein the ethylene amine is ethylene diamine.
4. The method of claim 1 wherein the solution is a solution of potassium tertiary butoxide in ethylene diamine.
5. The method of claim 4 wherein the acetal is dimethallylidene pentaerythritol.

* * * * *